United States Patent [19]

Gleason et al.

[11] Patent Number: 5,135,938
[45] Date of Patent: Aug. 4, 1992

[54] LEUKOTRIENE ANTAGONISTS

[75] Inventors: John G. Gleason, Downingtown; Ralph F. Hall; Irene Uzinskas, both of Villanova, all of Pa.

[73] Assignee: SmithKline Beecham Corporation, Philadelphia, Pa.

[21] Appl. No.: 502,007

[22] Filed: Mar. 30, 1990

Related U.S. Application Data

[62] Division of Ser. No. 66,592, Jun. 24, 1987, abandoned.

[51] Int. Cl.$^5$ ................ C07D 285/125; A61K 31/41
[52] U.S. Cl. .................... 514/363; 548/136; 548/251
[58] Field of Search .............. 548/136; 514/363

[56] References Cited

U.S. PATENT DOCUMENTS 4,927,822  5/1990  Brown .................. 514/236.2

FOREIGN PATENT DOCUMENTS 59-161366  9/1984  Japan .................. 548/136

Primary Examiner—Robert Gerstl
Attorney, Agent, or Firm—James M. Kanagy; Stuart R. Suter; Edward T. Lentz

[57] ABSTRACT

Leukotriene antagonist thiadiazoles have been prepared.

13 Claims, No Drawings

LEUKOTRIENE ANTAGONISTS

This is a division of application Ser. No. 07/066,592, filed Jun. 24, 1987 now abandoned.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

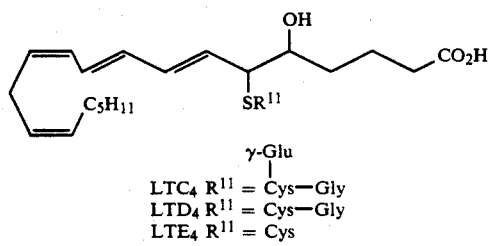

$LTC_4$ $R^{11}$ = Cys—Gly (γ-Glu)
$LTD_4$ $R^{11}$ = Cys—Gly
$LTE_4$ $R^{11}$ = Cys

Leukotrienes are a group of eicosanoids formed from arachidonic acid metabolism via the lipoxygenase pathway. These lipid derivatives originate from $LTA_4$ and are of two types: (1) those containing a sulfido-peptide side chain ($LTC_4$, $LTD_4$, and $LTE_4$), and (2) those that are nonpeptidic ($LTB_4$). Leukotrienes comprise a group of naturally occurring substances that have the potential to contribute significantly to the pathogenesis of a variety of inflammatory and ischemic disorders. The pathophysiological role of leukotrienes has been the focus of recent intensive studies.

As summarized by Lefer, A. M., *Biochemical Pharmacology*, 35, 2, 123–127 (1986), both the peptide and non-peptide leukotrienes exert microcirculatory actions, promoting leakage of fluid across the capillary endothelial membrane in most types of vascular beds. $LTB_4$ has potent chemotactic actions and contributes to the recruitment and adherence of mobile scavenger cells to the endothelial membrane. $LTC_4$, $LTD_4$ and $LTE_4$ stimulate a variety of types of muscles. $LTC_4$ and $LTD_4$ are potent bronchoconstrictors and effective stimulators of vascular smooth muscle. This vasoconstrictor effect has been shown to occur in pulmonary, coronary, cerebral, renal, and mesenteric vasculatures.

Leukotrienes have been implicated in a number of pulmonary diseases. Leukotrienes are known to be potent bronchoconstrictors in humans. $LTC_4$ and $LTD_4$ have been shown to be potent and selective peripheral airway agonists, being more active than histamine. [See Drazen, J. M. et al., *Proc. Nat'l. Acad. Sci. USA*, 77, 7, 4354–4358 (1980)]. $LTC_4$ and $LTD_4$ have been shown to increase the release of mucus from human airways in vitro. [See Marom, Z. et al., *Am. Rev. Respir. Dis.*, 126, 449–451 (1982)]. The leukotriene antagonists of the present invention can be useful in the treatment of allergic or non-allergic bronchial asthma or pulmonary anaphylaxis.

The presence of leukotrienes in the sputum of patients having cystic fibrosis, chronic bronchitis, and bronchiectasis at levels likely to have pathophysiological effects has been demonstrated by Zakrzewski et al. [See Zakrzewski, J. T. et al., *Prostaglandins*, 28, 5, 641 (1984).] Treatment of these diseases constitutes additional possible utility for leukotriene antagonists.

Leukotrienes have been identified in the nasal secretions of allergic subjects who underwent in vivo challenge with specific antigen. The release of the leukotrienes was correlated with typical allergic signs and symptoms. [See Creticos, P. S. et al., *New England J. of Med.*, 310, 25, 1626–1629 (1984).] This suggests that allergic rhinitis is another area of utility for leukotriene antagonists.

The role of leukotrienes and the specificity and selectivity of a particular leukotriene antagonist in an animal model of the adult respiratory distress syndrome was investigated by Snapper et al. [See Snapper, J. R. et al., *Abstracts of Int'l Conf. on Prostaglandins and Related Comp.*, Florence, Italy, p. 495 (June 1986.)] Elevated concentrations of $LTD_4$ were shown in pulmonary edema fluid of patients with adult respiratory distress syndrome. [See Matthay, M. et al., *J. Clin. Immunol.*, 4, 479–483 (1984).] Markedly elevated leukotriene levels have been shown in the edema fluid of a patient with pulmonary edema after cardiopulmonary bypass. [See Swerdlow, B. N., et al., *Anesth. Analg.*, 65, 306–308, (1986).] LTC and LTD have also been shown to have a direct systemic arterial hypotensive effect and produce vasoconstriction and increased vasopermeability. [See Drazen et al., ibid.] This suggests leukotriene antagonists can also be useful in the areas of adult respiratory distress syndrome, pulmonary edema, and hypertension.

Leukotrienes have also been directory or indirectly implicated in a variety of non-pulmonary diseases in the ocular, dermatologic, cardiovascular, renal, trauma, inflammatory, carcinogenic and other areas.

Further evidence of leukotrienes as mediators of allergic reactions is provided by the identification of leukotrienes in tear fluids from subjects following a conjunctival provocation test and in skin blister fluids after allergen challenge in allergic skin diseases and conjunctival mucosa. [See Bisgaard, H. et al., *Allergy*, 40, 417–423 (1985).] Leukotriene immunoreactivity has also been shown to be present in the aqueous humor of human patients with and without uveitis. The concentrations of leukotrienes were sufficiently high that these mediators were expected to contribute in a meaningful way to tissue responses. [See Parker, J. A. et al., Arch Ophthalmol, 104, 722–724 (1986).] It has also been demonstrated that psoriatic skin has elevated levels of leukotrienes. [See Ford-Hutchinson, *J. Allergy Clin. Immunol.*, 74, 437–440 (1984).] Local effects of intracutaneous injections of synthetic leukotrienes in human skin were demonstrated by Soter et al. [(See Soter et al., *J. Clin. Invest Dermatol*, 80, 115–119 (1983).] Cutaneous vasodilation with edema formation and a neutrophil infiltrate were induced. Leukotriene synthesis inhibitors or leukotriene antagonists can also be useful in the treatment of ocular or dermatological diseases such as allergic conjunctivitis, uveitis, allergic dermatitis or psoriasis.

Another area of utility for leukotriene antagonists is in the treatment of cardiovascular diseases. Since peptide leukotrienes are potent coronary vasoconstrictors, they are implicated in a variety of cardiac disorders including arrhythmias, conduction blocks and cardiac depression. Synthetic leukotrienes have been shown to be powerful myocardial depressants, their effects consisting of a decrease in contractile force and coronary flow. The cardiac effects of $LTC_4$ and $LTD_4$ have been shown to be antagonized by a specific leukotriene antagonist, thus suggesting usefulness of leukotriene antagonists in the areas of myocardial depression and cardiac anaphylaxis. [See Burke, J. A. et al., *J. Pharmacology and Experimental Therapeutics*, 221, 1, 235-241 (1982).]

$LTC_4$ and $LTD_4$ have been measured in the body fluids of rats in endotoxic shock, but are rapidly cleared from the blood into the bile. Thus leukotrienes are formed in ischemia and shock. Specific inhibitors of leukotriene biosynthesis reduce the level of leukotrienes and therefore reduce manifestations of traumatic shock, endotoxic shock, and acute myocardial ischemia. Leukotriene receptor antagonists have also been shown to reduce manifestations of endotoxic shock and to reduce extension of infarct size. Administration of peptide leukotrienes has been shown to produce significant ischemia or shock. [See Lefer, A. M., *Biochemical Pharmacology*, 35, 2, 123-127 (1986).] Thus further areas of utility for leukotriene antagonists can be the treatment of myocardial ischemia, acute myocardial infarction, salvage of ischemic myocardium, angina, cardiac arrhythmias, shock and atherosclerosis.

Leukotriene antagonists can also be useful in the area of renal ischemia or renal failure. Bard et al. have shown that $LTC_4$ produces significant elevation of mean arterial pressure and reductions in cardiac output and renal blood flow, and that such effects can be abolished by a specific leukotriene antagonist. [See Badr, K. F. et al., *Circulation Research*, 54, 5, 492-499 (1984).] Leukotrienes have also been shown to have a role in endotoxin-induced renal failure and the effects of the leukotrienes selectively antagonized in this model of renal injury. [See Badr, K. F. et al., *Kidney International*, 30, 474-480 (1986).] $LTD_4$ has been shown to produce local glomerular constrictor actions which are prevented by treatment with a leukotriene antagonist. [See Badr, K. F. et al., *Kidney International*, 29, 1, 328 (1986).] $LTC_4$ has been demonstrated to contract rat glomerular mesangial cells in culture and thereby effect intraglomerular actions to reduce filtration surface area. [See Dunn, M. J. et al., *Kidney International*, 27, 1, 256 (1985).] Thus another area of utility for leukotriene antagonists can be in the treatment of glomerulonephritis.

Leukotrienes have also been indicated in the area of transplant rejection. An increase in cardiac and renal allograft survival in the presence of a leukotriene receptor antagonist was documented by Foegh et al. [See Foegh, M. L. et al. *Advances in Prostaglandin, Thromboxane, and Leukotriene Research*, 13, 209-217 (1985).] Rejection of rat renal allografts was shown to produce increased amounts of $LTC_4$. [See Coffman, T. M. et al., *Kidney International*, 29, 1, 332 (1986).]

A further area of utility for leukotriene antagonists can be in treatment of tissue trauma, burns, or fractures. A significant increase in the production of cysteinyl leukotrienes was shown after mechanical or thermal trauma sufficient to induce tissue edema and circulatory and respiratory dysfunction. [See Denzlinger, C. et al., *Science*, 230, 330-332 (1985).]

Leukotrienes have also been shown to have a role in acute inflammatory actions. $LTC_4$ and $LTD_4$ have potent effects on vascular caliber and permeability and $LTB_4$ increases leukocyte adhesion to the endothelium. The arteriolar constriction, plasma leakage, and leukocyte adhesion bear close resemblance to the early events in acute inflammatory reactions. [See Dahlen, S. E. et al., *Proc. Natl. Acad. Sci. USA*, 78, 6, 3887-3891 (1981).] Mediation of local homeostasis and inflammation by leukotrienes and other mast cell-dependent compounds was also investigated by Lewis et al. [See Lewis, R. A. et al., *Nature*, 293, 103-108 (1981).] Leukotriene antagonists can therefore be useful in the treatment of inflammatory diseases including rheumatoid arthritis and gout.

Cysteinyl leukotrienes have also been shown to undergo enterohepatic circulation, and thus are indicated in the area of inflammatory liver disease. [See Denzlinger, C. et al., *Prostaglandins Leukotrienes and Medicine*, 21, 321-322 (1986).] Leukotrienes can also be important mediators of inflammation in inflammatory bowel disease. [See Peskar, B. M. et al., *Agents and Actions*, 18, 381-383 (1986).] Leukotriene antagonists thus can be useful in the treatment of inflammatory liver and bowel disease.

Leukotrienes have been shown to modulate IL-1 production by human monocytes. [See Rola-Pleszczynski, M. et al., *J. immun.*, 135, 6, 3958-3961 (1985).] This suggests that leukotriene antagonists may play a role in IL-1 medicated functions of monocytes in inflammation and immune reactions.

$LTA_4$ has been shown to be a factor in inducing carcinogenic tumors and is considered a link between acute immunologic defense reactions and carcinogenesis. Leukotriene antagonists can therefore possibly have utility in treatment of some types of carcinogenic tumors. [See Wischnewsky, G. G. et al. *Anticancer Res.* 5, 6, 639 (1985).]

Leukotrienes have been implicated in gastric cytodestruction and gastric ulcers. Damage of gastrointestinal mucosa because of potent vasoconstriction and stasis of blood flow is correlated with increased levels of $LTC_4$. Functional antagonism of leukotriene effects may represent an alternative in treatment of mucosal injury. [See Dreyling, K. W. et al., *British J. Pharmacology*, 88, 236P (1986), and Peskar, B. M. et al *Prostaglandins*, 31, 2, 283-193 (1986).] A leukotriene antagonist has been shown to protect against stress-induced gastric ulcers in rats. [See Ogle, C. W. et al., *IRCS Med. Sci.*, 14, 114 (1986).]

Other areas in which leukotriene antagonists can have utility because leukotrienes are indicated as mediators include prevention of premature labor [See Clayton, J. K. et al., *Proceedings of the BPS*, 573P, 17-19 Dec. 1984]; treatment of migraine headaches [See Gassaniga, P. P. et al., *Abstracts Int'l Conf. on Prostaglandins and Related Comp.*, 121, Florence, Italy (June 1986)]; and treatment of gallstones [See Doty, J. E. et al., *Amer. J. of Surgery*, 145, 54-61 (1983) and Marom, Z. et al., *Amer. Rev. Respir. Dis.*, 126, 449-451 (1982).]

By antagonizing the effects of $LTC_4$, $LTD_4$ and $LTE_4$ or other pharmacologically active mediators at the end organ, for example, airway smooth muscle, the compounds and pharmaceutical compositions of the instant invention are valuable in the treatment of diseases in subjects, including human or animals, in which leukotrienes are a key factor.

SUMMARY OF THE INVENTION

This invention relates to compounds represented by structural formula (I)

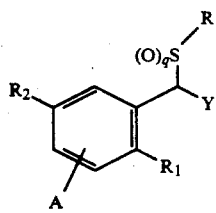

wherein
q is 0, 1, or 2;
$R_1$ is $(L)_a$—$(CH_2)_b$—$(T)_c$—B
a is 0 or 1;
b is 3 to 14;
c is 0 or 1;
L and T are independently sulfur, oxygen, or $CH_2$ with the proviso that L and T are not sulfur when q is 1 or 2; and
B is $C_{1-4}$ alkyl, ethynyl, trifluoromethyl, isopropenyl, furanyl, thienyl, cyclohexyl or phenyl optionally monosubstituted with Br, Cl, $DF_2$, $C_{1-4}$ alkoxy, $C_{1-4}$ alkyl, methylthio, or trifluoromethylthio;
$R_2$ and A are independently selected from H, $CF_2$, $C_{1-4}$alkyl, $C_{1-4}$ alkoxy, F, Cl, Br, I, OH, $NO_2$ or $NH_2$;
or $R_1$ and A are H and
$R_2$ is $(L)_1$—$(CH_2)_b$—$(T)_c$—B wherein a, b, c, L, T, and B are as defined above;
Y is $COR_3$ or

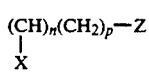

wherein
$R_3$ is OH, $NH_2$, aryloxy, or $C_{1-6}$ alkoxy;
n is 0 or 1;
p is 0, 1 or 2;
S is H, OH, $C_{1-4}$ alkoxy, or F; and
Z is $COR_3$, or tetrazolyl;

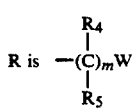

m is 0 to 6
$R_4$ and $R_5$ are independently hydrogen or $C_{1-4}$alkyl at any position when m is not 0;
W is a 5-membered heteroaryl ring selected from tetrazole, thiazole, triazole, thiophene, furan, oxazole, thiadiazole, pyrrole, or pyrazole, each group unsubstituted or substituted with one to three

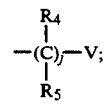

$R_4$ and $R_5$ are as defined above,
j is 0 to 6, and
V is hydrogen, $C_{1-4}$alkyl, $COR_3$, $SO_3H$, $SO_2H$, $SO_2NH_2$, $COCH_2OH$, $CHOHCH_2OH$, or tetrazolyl with $R_3$ as defined above;
or a pharmaceutically acceptable salt thereof.

This invention further relates to the ester or diester derivatives of the compounds of Formula (I).

This invention includes all stereoisomers, racemates, or mixtures thereof. For example, W can be 1,2,3-triazole; 1,3,4-triazole; 1,2,3-thiadiazole, 1,3,4-thiadiazole, and other possible stereoisomers.

This invention further relates to pharmaceutical compositions comprising a pharmaceutical carrier or diluent and a nontoxic amount of the compound of formula (I). Such compositions are useful for inhibiting the effects of leukotrienes and in treating diseases in which leukotrienes are a factor.

This invention further relates to pharmaceutical compositions comprising a pharmaceutical carrier or diluent and nontoxic amounts of a compound of formula (I) and a histamine $H_1$-receptor antagonist. Such compositions are useful in inhibiting antigen-induced respiratory anaphylaxis.

This invention further relates to methods for inhibiting the effects of leukotrienes. This invention also relates to methods for inhibiting antigen-induced respiratory anaphylaxis comprising administration of an effective amount of the above-described pharmaceutical compositions.

DETAILED DESCRIPTION OF THE INVENTION

The compounds of this invention are represented by the following general structural formula (I)

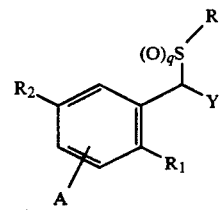

wherein
q is 0, 1, or 2;
$R_1$ is $(L)_a$—$(CH_2)_b$—$(T)_c$—B;
a is 0 or 1;
b is 3 to 14,
c is 0 or 1;
L and T are independently oxygen, sulfur, or $CH_2$ with the proviso that L and T are not sulfur when q is 1 or 2; and
B is $C_{1-4}$ alkyl, ethynyl, trifluoromethyl, isopropenyl, uranyl, thienyl, cyclohexyl, or phenyl optionally monosubstituted with Br, Cl, $CF_3$, $C_{1-4}$ alkoxy, $C_{1-4}$ alkyl, methylthio, or trifluoromethylthio;
$R_2$ and A are independently selected from H, $CF_3$, $C_{1-4}$alkyl, $C_{1-4}$alkoxy, F, Cl, Br, I, OH, $NO_2$ or $NH_2$;

or $R_1$ and A are H and
$R_2$ is $(L)_a$—$(CH_2)_b$—$(T)_c$—B wherein a, b, c, L, T, and B are as defined above;
Y is $COR_3$ or

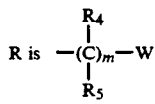

wherein
$R_3$ is OH, $NH_2$, aryloxy or $C_{1-6}$ alkoxy;
n is 0 or 1;
p is 0, 1 or 2;
X is H, OH, $C_{1-4}$alkyl, $C_{1-4}$alkoxy or F; and
Z is $COR_3$, or tetrozolyl;

$$R \text{ is } -\underset{R_5}{\overset{R_4}{(C)_m}}-W$$

m is 0 to 6
$R_4$ and $R_5$ are independently hydrogen or $C_{1-4}$alkyl at any position when m is not 0; and
W is a 5-membered ring heteroaryl group selected from tetrazole, thiazole, triazole, thiophene, furan, oxazole, thiadiazole, pyrrole, imidazole, or pyrazole, each group unsubstituted or substituted with one to three $$-\underset{R_5}{\overset{R_4}{(C)_j}}-V;$$

wherein $R_4$ and $R_5$ are as defined above,
j is 0 to 6; and
V is hydrogen, $C_{1-4}$alkyl, $COR_3$, $SO_3H$, $SO_2H$, $SO_2NH_2$, $COCH_2OH$, $CHOHCH_2OH$, or tetrazolyl, with $R_3$ as defined above;
or a pharmaceutically acceptable salt thereof.

This invention includes all stereoisomers, racemates, or mixtures thereof. For example, W can be 1,2,3-triazole; 1,3,4-triazole; 1,2,3-thiadiazole, 1,3,4-thiadiazole, and other possible stereoisomers.

The compounds of this invention further comprise the ester and diester derivatives of the compounds of Formula (I).

A subgeneric class of these compounds are those represented by structural formula (I) wherein Y is $CO_2H$. Particular members of this subgeneric class are exemplified by the following compounds:

(1) 2-(2-Dodecylphenyl)-2-[(1-carboxymethyl-5-tetrazolyl]thio]acetic acid;

(2) 2-(2-Dodecylphenyl)-2-]]1-(3-carboxypropyl)-5-tetrazolyl]thio]acetic acid;

(3) 2-(2-Dodecylphenyl)-2-[(1-sulfomethyl-5-tetrazolyl)thio]acetic acid;

(4) 2-(2-Dodecylphenyl)-2-[(1-methyl-5-tetrazolyl)-thio]acetic acid;

(5) 2-[2-(8-Phenyloctyl)phenyl]-2-[[1-(3-carboxypropyl)-5-tetrazolyl]thio]acetic acid;

(6) 2-[2-(Tetrazol-5-yl)ethylthio]-2-(2-dodecylphenyl)acetic acid; and (7) 2-(2-Dodecylphenyl)-2-(5-carboxy-4-methyl-2-thiazolylthio)acetic acid.

A second subgeneric class of these compounds are those represented by structural formula (I) where Y is $CH_2COOH$. Particular members of this subgeneric class are exemplified by the following compounds:

(1) 3-(2-Dodecylphenyl)-3-[[1-(3-carboxypropyl)-5-tetrazolyl]propanoic acid;

(2) 3-[2-(8-Phenyloctyl)phenyl]-3-[(1-carboxymethyl-5-tetrazolyl)thio]propanoic acid; and (3) 3-[2-(8-Phenyloctyl)phenyl]-3-[[1-(3-carboxypropyl)-5-tetrazolyl]thio]propanoic acid.

A third subgeneric class of these compounds are those represented by structural formula (I) where Y is $$\underset{OH}{\overset{}{CHCOOH.}}$$

Particular member of this subgeneric class are exemplified by the following compounds:

(1) 3-[2-(8-phenyloctyl)phenyl]-3-[[1-(3-carboxypropyl)-5-tetrazolyl]thio]-2-hydroxypropanoic acid; and (2) 3-[2-(8-phenyloctyl)phenyl]-3-[(1-carobxymethyl-5-tetrazolyl)thio]-2-hydroxypropanoic acid.

Some of the compounds of formula (I) contain one or two asymmetric center. This leads to the possibility of two or four stereoisomers for each compound. The present invention includes all such stereoisomers, racemates, or mixtures thereof. The compounds of the present invention, depending upon their structure, are capable of forming salts with known pharmaceutically acceptable bases, according to procedures well known in the art. Such acceptable bases include inorganic and organic bases, such as ammonia, arginine, organic amines, alkaline earth and alkali metal bases. Of particular utility are the dipotassium, magnesium, calcium, diammonium and disodium salts of the diacid compounds of formula (I).

The compounds of the formula (I) wherein Y is $CO_2H$ are conveniently prepared from an aldehyde precursor of the following structural formula (II)

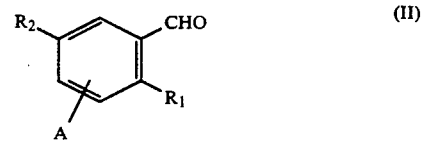 (II)

wherein A, $R_1$ and $R_2$ are described above. A compound of formula (II) is treated with trimethylsilyl cyanide in the presence of zinc iodide at low temperatures in an inert solvent to form the trimethylsilyl-protected cyanohydrin. Treatment of this with gaseous hydrogen chloride in methanol provides the methyl 2-chloroacetate with thionyl chloride. This valuable intermediate is then reacted with an appropriate thiol selected to give, after removal of ester protective groups, the desired product of formula (I).

The compounds of the formula (I) wherein Y is $CH(X)CO_2H$, wherein X is H, $C_{1-4}$ alkyl, or $C_{1-4}$ alkoxy, are prepared by reacting the appropriate aldehyde of the formula (II) and an esterified bromoacetate, conveniently t-butyl bromoacetate, with a mixture of diethyl aluminum chloride, zinc dust and a catalytic amount of cuprous bromide at low temperatures in an inert solvent to give the esterified 3-hydroxy-propionate derivative which is reacted directly with a substituted thiol in trifluoroacetic acid. Alternatively, a mixture of trimethyl borate and zinc in tetrahydrofuran may be used to prepare the 3-hydroxypropionate derivative. By employing an esterified 2-bromo-propionate in the above reaction with an aldehyde (II), the compounds of the formula (I) wherein Y is $CH(CH_3)CO_2H$ are obtained.

Alternatively, the compounds of the formula (I) wherein Y is $CH(X)CO_2H$ wherein X is H, $C_{1-4}$ alkyl, $C_{1-4}$ alkoxy, or fluoro are prepared from a propionate precursor of the following structural formula (IV)

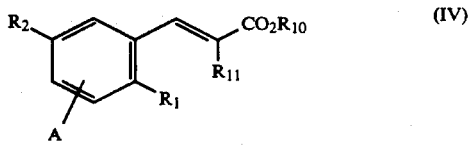

wherein A, $R_1$ and $R_2$ are described above, $R_{10}$ is a conventional ester protective group, such as t-butyl or $C_{1-4}$ alkyl, and $R_{11}$ is hydrogen, $C_{1-4}$ alkyl, $C_{1-4}$ alkoxy, or fluoro. A compound of formula (IV) is reacted with a mixture of alkali metal alkoxide, such as sodium methoxide, and an appropriate thiol to give, after removal of the ester protective group, the desired product of formula (I).

The propionate precursors of formula (IV) are prepared from the corresponding aldehydes of formula (II) by general procedures such as reaction with an alkyl (triphenylphosphoranylidene)acetate or by conversion of the aldehyde to a 3-hydroxypropionate derivative, as described above, followed by an elimination reaction to form the double bond. Additionally, the propionate precursor is obtained from a 3-methanesulfonyloxypropionate derivative by treatment with triethylamine.

The compounds of the formula (I) wherein Y is $CH(OH)(CH_2)_pCO_2H$ are prepared from an epoxide precursor of the following structural formula (V)

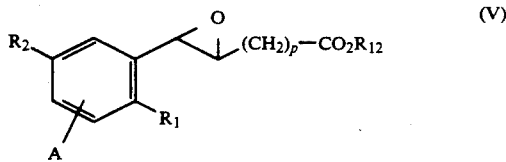

wherein A, $R_1$ and $R_2$ are described above, p is 0, 1 or 2 and $R_{12}$ is a conventional ester protective group, such as t-butyl or $C_{1-4}$ alkyl such as methyl or ethyl. A compound of formula (V) is reacted in an inert solvent with triethylamine and the appropriate thiol selected to give, after removal of ester protective groups, a desired product of formula (I).

The epoxide precursors of formula (V) where p is 2 are prepared by reaction of the Grignard derivative of a bromobenzene compound of the formula (VI)

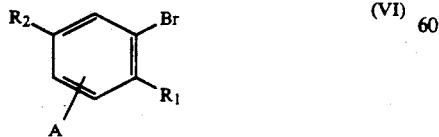

with acrolein to give the corresponding enol derivative which is treated with a trialkylorthoacetate, followed by epoxidation using m-chloroperbenzoic acid.

The epoxide precursors of formula (V) where p is 1 can be prepared by Arndt-Eistert homologation of the compound where p is 0 and $R_{12}$ is H.

The epoxide precursors of formula (V) where p is O are prepared by reaction of an aldehyde of the formula (II) with a lower alkyl chloroacetate and an alkali metal alkoxide, such as sodium methoxide in an appropriate solvent such as diethyl ether or methylene chloride.

The compounds of the formula (I) wherein Y is $(CH_2)_3CO_2H$ are prepared from a tetrahydro-4H-pyran-2-one precursor of the following structural formula (VII)

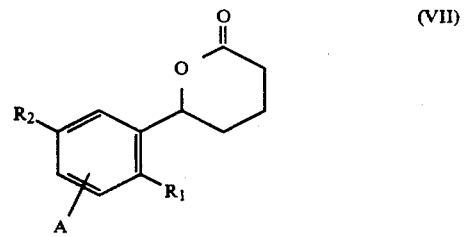

wherein A, $R_1$ and $R_2$ are described above. A compound of formula (VII) is reacted with a mixture of zinc iodide and a substituted thiol in an inert solvent or with a substituted thiol in trifluoroacetic acid to give, after removal of any ester protective group, a product of formula (I).

The tetrahydro-4H-pyran-2-one precursors of formula (VII) are prepared by reaction of the Grignard derivative of the bromobenzene compound of formula (VI) with chlorotitanium triisopropoxide followed by reaction with 5-oxovalerate alkyl ester.

The aldehydes of the formula (II) are known or readily prepared utilizing the general procedures described as follows.

The aldehyde precursors to the compounds of the formula (I) wherein $R_1$ is, for example, an alkyl radical containing 8 to 13 carbon atoms are prepared from the appropriate 2-alkylphenyl-4-,4-dimethyloxazoline [see Meyers et al. J. Org. Chem., 43 1372 (1978)].

The aldehyde precursors of the compounds of the formula (I) wherein $R_1$ is, for example, an alkoxy radical containing 7 to 12 carbon atoms are prepared by the O-alkylation of the appropriate 2-hydroxybenzaldehyde with the corresponding alkylating agent by standard methods.

The thioalkyl containing aldehyde precursors of the compounds of the formula (I) are prepared by the reaction of the appropriately substituted o-haloalkylthiobenzene (for example, a compound of formula (III):

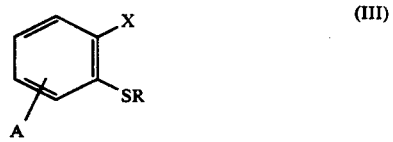

wherein X is halo and R is alkyl, with magnesium and dimethylformamide by standard methods.

The phenylthioalkyl containing aldehyde precursors of the compounds of the formula (I) are prepared by the reaction of the appropriately substituted haloalkylbenzaldehyde with a thiophenol and triethylamine.

The heteroaryl mercaptan precursors necessary to prepare the compounds of formula (I) are known compounds and are conveniently prepared employing standard chemical reactions. The mercapto derivatives of these precursors are prepared according to known methods. For example, 5-(2-mercaptoethyl)tetrazole can be prepared by adding β-merceptopropionitrile to a mixture of sodium azide and aluminium chloride in tetrahydrofuran. The preparation of tetrazolthiol compounds with various substituents is described in Berges U.S. Pat. Nos. 4,048,311, 4,220,644; and 4,286,089. The preparation of triazolthiols and thiadiazolthiols with various substituents is taught in Berges U.S. Pat. Nos. 3,868,369 and 3,989,694. These mercaptans are reacted as described above to yield compounds of formula (I).

Appropriate modifications of the general processes disclosed, and as further described in the Examples provided hereinbelow, furnish the various compounds defined by formula (I).

The leukotriene antagonist activity of the compounds of this invention is measured by the ability of the compounds to inhibit the leukotriene induced contraction of guinea pig tracheal tissues in vitro. The following methodology was employed:

In vitro: Guinea pig (adult male albino Hartley strain) tracheal spiral strips of approximate dimensions 2 to 3 mm cross-sectional width an 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1M) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the percentage of the maximum response obtained to a reference agonist, carbachol (10M).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The -log $K_B$ value for the test compound was determined by the following equations:

1. $\dfrac{EC_{30} \text{ (presence of test compound)}}{EC_{30} \text{ (presence of vehicle control)}} = \text{dose ratio} = X$ 2. $K_B$ = concentration of test compound/(X−1)

The compounds of this invention possess biosignificant antagonist activity against leukotrienes. The antagonist activity of representative compounds of this invention is tabulated below in Table I (other data appears in the preparative examples). The -log $K_B$ values were calculated from the above test protocol. Where compounds were tested more than once, the -log $K_B$ values given herein represent the current average data.

TABLE I

| | | Leukotriene Antagonist Activity | | | |
| | | Compounds of Formula (I)* | | | In Vitro |
| −W | m | −(C)jR₄R₅V | $R_1$ | Y | -Log $K_B$ |
|---|---|---|---|---|---|
| 5-tetrazolyl | 0 | 1-$CH_2COOH$ | $C_{12}H_{25}$ | $CO_2H$ | 6.1 |
| 5-tetrazolyl | 0 | 1-$CH_2SO_3H$ | $C_{12}H_{25}$ | $CO_2H$ | 6.4 |
| 5-tetrazolyl | 0 | 1-$CH_3$ | $C_{12}H_{25}$ | $CO_2H$ | 5.8 |
| 5-tetrazolyl | 0 | 1-$(CH_2)_3COOH$ | $C_{12}H_{25}$ | $CO_2H$ | 7.4 |
| 5-tetrazolyl | 0 | 1-$(CH_2)_3COOH$ | $(CH_2)_8Ph$ | $CO_2H$ | 6.0 |
| 5-tetrazolyl | 0 | 1-$(CH_2)_3COOH$ | $C_{12}H_{25}$ | $CH_2CO_2H$ | 6.6 |
| 5-tetrazolyl | 0 | 1-$CH_2COOH$ | $(CH_2)_8Ph$ | $CH_2CO_2H$ | 6.3 |
| 5-tetrazolyl | 0 | 1-$(CH_2)_3COOH$ | $(CH_2)_8Ph$ | $CH_2CO_2H$ | 6.0 |
| 5-tetrazolyl | 2 | 1-H | $C_{12}H_{25}$ | $CO_2H$ | 6.5 |
| 5-tetrazolyl | 0 | 1-$(CH_2)_3COOH$ | $(CH_2)_8Ph$ | $CH(OH)CO_2H$ | 7.0 |
| 5-tetrazolyl | 0 | 1-$CH_2COOH$ | $(CH_2)_8Ph$ | $CH(OH)CO_2H$ | 7.0 |
| 2-thiazolyl | 0 | 4-$CH_3$, 5-COOH | $C_{12}H_{25}$ | COOH | 6.7 |

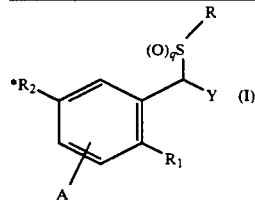

wherein $R_4$ and $R_5$ are H, W is optionally substituted with $-(C)_5-R_4R_5-Y$; $R_2$ and A are H; and q is 0

Pharmaceutical compositions of the present invention comprise a pharmaceutical carrier or diluent and an amount of a compound of the formula (I) or a pharmaceutically acceptable salt, such as an alkali metal salt thereof, sufficient to produce the inhibition of the effects of leukotrienes, such as symptoms of asthma and other hypersensitivity diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid paraffins and mixtures thereof with water; for solid systems, lactose, kaolin and mannitol; and for aerosol systems, dichlorodifluoromethane, chlorotrifluoroethane and compressed carbon dioxide propellants. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally, topically, orally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in lesser, equal or greater amounts than the solid active ingredient.

For parenteral administration the pharmaceutical composition will be in the form of a sterile injectable liquid such as an ampule or an aqueous or nonaqueous liquid suspension.

For topical administration the pharmaceutical composition will be in the form of a cream or ointment.

Usually a compound of formula I is administered to an animal subject, including humans, in a composition comprising a nontoxic amount sufficient to produce an inhibition of the symptoms of an allergic response. When employed in this manner, the dosage of the composition is easily determined by those skilled in the art and are generally selected from the range of from 350 mg. to 700 mg. of active ingredient for each administration. For convenience, equal doses will be administered 1 to 4 times daily with the daily dosage regimen being selected from about 350 mg. to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response which comprises administering to an animal subject a therapeutically effective amount for producing said inhibition of a compound of formula I, preferably in the form of a pharmaceutical composition. The administration may be carried out in dosage units at suitable intervals or in single doses as needed. Usually this method will be practiced when relief of allergic symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

Compounds of this invention, alone and in combination with a histamine $H_1$-receptor antagonist, inhibit antigen induced contraction of isolated, sensitized guinea pig trachea (a model of respiratory anaphylaxis).

Pharmaceutical compositions, as described hereinabove, of the present invention also comprise a pharmaceutical carrier or diluent and a combination of a compound of the formula (I) or a pharmaceutically acceptable salt thereof, and a histamine $H_1$-receptor antagonist in amounts sufficient to inhibit antigen-induced respiratory anaphylaxis. Examples of histamine $H_1$-receptor antagonists include mepyramine, 2-[4-(5-bromo-3-methyl-pyrid-2-yl)butylamino]-5-[(6-methyl-pyrid-3-yl) methyl]-4-pyrimidone and other known $H_1$-receptor antagonists. The above-defined dosage of a compound of formula I is conveniently employed for this purpose with the known effective dosage for the histamine $H_1$-receptor antagonist. The methods of administration described above for the single active ingredient can similarly be employed for the combination with a histamine $H_1$-receptor antagonist.

The following examples illustrate the preparation of the compounds of this invention and their incorporation into pharmaceutical compositions and as such are not to be considered as limiting the invention set forth in the claims appended hereto.

EXAMPLE 1

Preparation of
2-(2Dodecylphenyl)-2-Dodecylphenyl)-2[(1-methyl-5-tetrazolyl)thio]acetic acid (a) 2-(2-Dodecylphenyl)-4,4-dimethyloxazoline To freshly prepared dodecylmagnesium bromide (from 30.13 mmol of dodecyl bromide and 26.20 mmol of magnesium) in distilled tetrahydrofuran (50 ml) was added 2-(2-methoxyphenyl)-4,4-dimethyloxazoline [A. I. Meyers et al., *J. Org. Chem.*, 43, 1372 (1978)] (17.88 mmol) in tetrahydrofuran (30 ml). The resultant yellow solution was stirred under argon at ambient temperature for 20 hours. The solution was cooled in an ice water bath and quenched with aqueous ammonium chloride (100 ml). The reaction product was extracted into diethyl ether (100 ml) and the organic phase was washed with saturated sodium chloride solution (50 ml) and then dried over anhydrous magnesium sulfate. Evaporation of the organic phase afforded a colorless oil which was purified by flash chromatography over silica gel with 5 percent ethyl acetate in hexane as eluant to afford the desired product as a pale yellow oil.

Analysis for $C_{23}H_{37}NO$: Calculated: C, 80.41; H, 10.85; N, 4.08. Found: C, 80.22; H, 10.56; N, 3.87.

(b) 2-(2-Dodecylphenyl)-3,4,4-trimethyloxazolinium iodide

A solution of the compound of Example 1(a) (17.2 mmol) in methyl iodide (20 ml) was refluxed under argon for 18 hours. The volatiles were removed under vacuum and the solid residue triturated with ethyl acetate (25 ml) to afford the desired product as white crystals (mp 78°–84° C.).

(c) 2-Dodecylbenzaldehyde

To an ice cold solution of the compound of Example 1(b) (10.0 mmol) in methanol (50 ml) over a period of 15 minutes was added in small portions sodium borohydride (10.0 mmol). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate. Evaporation of the extract afforded an oil which was dissolved in acetone (50 ml) and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil.

Analysis for $C_{19}H_{30}O$: Calculated: C, 83.15; H, 11.02. Found C, 82.59; H, 10.65.

(d) Methyl 2-(2-dodecylphenyl)-2-hydroxyacetate

The compound of Example 1(c) (17.2 mmol) was dissolved in methylene chloride (20 ml) and stirred at 0° C. under argon. Zinc iodide (1.87 mmol) was added, followed by the dropwise addition of trimethylsilyl cyanide (2.45 ml, 18.3 mmoles) dissolved in methylene chloride (30 ml). After 1 hour at 0° C. the ice bath was removed and the mixture stirred for 1 hour at room temperature. The solvent was stripped and methanol (100 ml) was added after the residue was cooled in an ice bath. Excess hydrogen chloride was bubbled into the solution while the mixture was stirred at ice bath temperature. The ice bath was then removed and the mixture stirred at room temperature for 18 hours. Water (20 ml) was added and the mixture stirred for 2 hours. The solvent was evaporated and the aqueous residue extracted with ethyl acetate. The combined organic phases were dried over anhydrous sodium sulfate, filtered and evaporated. The crude product was flash chromatographed on silica gel, eluted with 20% ethyl acetate/hexane, to give the product as a clear colorless liquid.

(e) Methyl 2-Chloro-2-(2-dodecylphenyl)acetate

The compound of Example 1(d) (12 mmol) was stirred under argon in an ice bath and thionyl chloride (20 ml) was added in a single portion. The ice bath was removed and the mixture was stirred under argon for 18 hours. The solvent was stripped and the residue was flash chromatographed on 200 grams of silica gel with 20% methylene chloride/carbon tetrachloride as eluant to give the product as a clear colorless liquid.

(f) Methyl 2-(2-Dodecylphenyl)-2-[(1-methyl-5-tetrazolyl)thio]acetate

The compound of Example 1(e) was mixed in an amount of 0.7 g (0.002 mol) with 0.37 g (0.0027 mol) of 5-mercapto1-methyltetrazole sodium salt, 1 ml of triethylamine and 20 ml of methylene chloride. The mixture was stirred at ambient temperature under argon for 3 days. The reaction mixture was washed with water, dried over anhydrous magnesium sulfate and filtered. The filtrate was concentrated under vacuum to yield 0.7 g of product.

(g) 2-(2-Dodecylphenyl)-2-](1-methyl-5-tetrazolyl)thio]acetic acid

The compound of Example 1(f) in an amount of 0.7 g (0.0016 mol)was dissolved in 5 ml of methanol, mixed with 0.4 g (0.01 mol) of sodium hydroxide, and stirred for 2 hours. The reaction mixture was concentrated under vacuum and the residual oil was redissolved in 5 ml. of water. The pH of the solution was adjusted to 4.8 or until a precipitate formed. The precipitate was filtered, redissolved in methylene chloride, washed with water, dried over anhydrous magnesium sulfate, filtered, and concentrated under vacuum. The resulting 0.3 g of oil was flash chromatographed on silica gel, with methylene chloride, 0.05% methanol, and 0.001% formic acid as eluent to yield 0.18 g of oil which solidified to a low melting wax.

Similarly, the following compounds are prepared according to the general method of Example 1 from the 2-(2-methoxyphenyl)-4,4-dimethyloxazoline and the appropriate alkyl halide:

2-(2-Tetradecylphenyl)-2-[(1-methyl-5-tetrazolyl)-thio]acetic acid; and 2-(2-Octylphenyl)-2-[(1-methyl-5-tetrazolyl)-thio]acetic acid.

EXAMPLE 2

Preparation of 2(2-Dodecylphenyl)-2[(1-carboxymethyl-5-tetrozolyl)-thio]acetic acid.

(a) Methyl 2-(2-Dodecylphenyl)-2[(1-carbethoxymethyl-5-tetrazolyl)thio]acetate

The compound of Example 1(e) (352 mg, 1 mmol), triethylamine (0.21 ml, 1.5 mmol) and 5-mercapto-1-carbethoxymethyltetrazole (250 mg. 1.33 mmol) were combined in 25 ml of methylene chloride. The mixture was stirred under argon at ambient temperature for 2 days. The solvent was stripped and the residue flash chromatographed on 50 grams of silica gel eluted with 15% ethyl acetate/hexane to give the product (500 mg, 99%) as a clear colorless liquid.

(b) 2-(2-Dodecylphenyl)-2-[2-(1-carobxymethyl-5-tetrazolyl)thio]acetic acid

The compound of Example 2(a) (260 mg, 0.52 mmol) was dissolved in 4.2 ml of methanol and stirred under argon in an ice bath. A 1 N solution of sodium hydroxide (2.1 ml, 2.1 mmol) was added. The ice bath was removed, and the mixture stirred for 1 hour at ambient temperature during which time a white precipitate formed. The methanol was evaporated and an additional 4 ml of water added to give a slightly turbid mixture which was stirred overnight at ambient temperature. The mixture was acidified with dilute hydrochloric acid, extracted with ethyl acetate, dried over anhydrous sodium sulfate, filtered and evaporated. The crude product was recrystallized from ethyl acetate/hexane to yield the desired product (204 mg. 86%) as a white crystalline solid with m.p. 147°-148° C.

Analysis for $C_{23}H_{34}N_4O_4S$— Calculated: C,59.72; H,7.41;; N,12.11. Found: C,59.61; H,7.27; N,12.15.

EXAMPLE 3

Preparation of 2-(2-Dodecylphenyl)-2-[[1-(3-carboxypropyl)-5-tetrazolyl]thio]acetic acid (a) Methyl 2-(2-dodecylphenyl)-2-[[1-(3-carboxypropyl)-5-tetrazolyl]thio]acetate The compound of Example 1(e) (325 mg, 1 mmol), triethylamine (0.42 ml, 3 mmol), 5-mercapto-1-(3-carboxypropyl)tetrazole (250 mg, 1.33 mmol) and 25 ml of methylene chloride were combined and stirred under argon at ambient temperature overnight. The solvent was stripped and the residue flash chromatographed on 50 grams of silica gel, eluted with 70:30:1 (hexane: ethyl acetate: formic acid) to yield the desired product (411 mg, 82%).

(b) 2-(2-Dodecylphenyl)-2-[[1-(3-carboxypropyl)-5-tetrazolyl]thio]acetic acid

The compound of Example 3(a) (411 mg, 0.82 mmol) was dissolved in 10 ml of methanol and stirred under argon in an ice bath. A 1 N solution of sodium hydroxide (3.2 ml, 3.2 mmol) was added dropwise, the ice bath removed and the mixture stirred overnight at ambient temperature. The solvent was stripped and the residue acidified with dilute hydrochloric acid at ice bath temperature. The crude product was extracted with ethyl acetate, dried over anhydrous sodium sulfate, filtered and evaporated. The residue was flash chromatographed on 50 grams of silica gel eluted with 30:70:1 (ethyl acetate: hexane:formic acid) followed by 50:50:1 (ethyl acetate:hexane:formic acid). Recrystallization from ethyl ether/hexane gave the desired product (285 mg, 71%) as a white crystalline solid with m.p. 86°-88° C.

Analysis for $C_{25}H_{38}N_4O_4S$— Calculated: C,61.20; H,7.81; N,11.42; S,6.53. Found: C,61.43; H,7.83; N,11.59; S,6.60.

EXAMPLE 4

Preparation of 2-(2-Dodecylphenyl)-2-[(1-sulfomethyl-5-tetrazolyl)thio]acetic acid ammonium salt hydrate The compound of Example 1(e) (200 mg, 0.57 mmol) and 5-mercapto-1-sulfomethyltetrazole disodium salt (136 mg, 0.57 mmol) were dissolved in 4 ml of dimethylformamide and stirred at ambient temperature overnight. The solvents were pumped off and the residue dissolved in 5 ml of water. A 1 N solution of sodium hydroxide (2 ml, 2 mmol) was added at 0° and the mixture stirred overnight at ambient temperature. The solvents were pumped off and the residue flash chromatographed on 50 grams of silica gel eluted with 6:3:1 (methylene chloride: ethanol: ammonium hydroxide). The solvents were stripped and the residue taken up in water and lyophilized to give the desired compound (180 mg 58%) as an amorphous white solid.

Analysis for $C_{22}H_{34}N_4O_5S_2 \cdot 2NH_3 \cdot 3/2 H_2O$— Calculated: C,47.21; H,7.74; N,15.01. Found: C,47.56; H,7.39; N 14.70.

EXAMPLE 5

Preparation of 2[2-(8Phenyloctyl)phenyl]-2-[[1-(3-carboxypropyl)-5-tetrazolyl]thio]acetic acid dipotassium salt hydrate (a) 2-(8-Phenyloctyl)benzaldehyde 8-Phenyloctyl bromide was prepared from 8-phenyloctanol, carbon tetrabromide and triphenylphosphine in methylene chloride. A solution of 8-phenyloctanoic acid (19.8 mmol) in sieve dried tetrahydrofuran (5 ml) was reduced with diborane in tetrahydrofuran (30 ml, 29.1 mmol) at 20° C. for 4 hours to give 8-phenyloctanol. To an ice cold solution of the octanol (ca. 19.8 mmol) and carbon tetrabromide (21.98 mmol) in methylene chloride (50 ml) was added triphenylphosphine (22.30 mmol) in methylene chloride (50 ml) and the resulting solution was stirred for 2.5 hours. The volatiles were evaporated and the residue was taken up in ether (100 ml), cooled in ice, and filtered. The filtrate was evaporated and distilled to afford 8-phenyloctyl bromide as an oil. To 8-phenyloctyl bromide and 21.27 mmol of magnesium) in distilled tetrahydrofuran (40 ml) was added 2-(2-methoxyphenyl)-4,4-dimethyloxazoline (17.10 mmol) in tetrahydrofuran (20 ml). After stirring for 24 hours, the reaction mixture was similarly worked up to yield 2-[2-(8-phenyloctyl)phenyl]-4,4-dimethyloxazoline as an oil. A solution of the oxazoline (11.58 mmol) in methyl iodide (20 ml) as refluxed under argon for 18 hours. Removal of the volatiles afforded the corresponding 3,4,4-trimethyloxazolinium iodide as a white solid (mp 76.5°-78° D.). To an ice cold solution of the iodide (9.46 mmol) in methanol (35 ml) was added in portions sodium borohydride (9.20 mmol). Treatment of the reaction mixture as in Example 1(c) results in the isolation of the desired product as an oil.

Analysis for $C_{21}H_{26}O$: Calculated: C, 85.67; H, 8.90. Found: C, 85.12, 85.22; H, 8.94, 8.96.

(b) Alternative preparation of 2-(8-phenyloctyl) benzaldehyde

A solution of 5-hexynyl alcohol (102 mmol) in pyridine (150 ml), under argon, was cooled to 0° C. and p-toluenesulfonyl chloride (204 mmol) was added. The reaction mixture was kept at about 4° C. for 18 hours, poured into ice-water and then taken up in ether. The ether extract was washed with cold 10% hydrochloric acid, water and brine. The organic layer was dried and concentrated in vacuo to give 5-hexynyl p-toluenesulfonate. A solution of phenylacetylene (97 mmol) in tetrahydrofuran (200 ml) containing a trace of triphenylmethane was cooled to 0° C. and then n-butyl lithium (37.3 ml of 2.6 mol in hexane) was added dropwise. The resulting solution was stirred at 0° C. for 10 minutes and hexamethylphosphoramide (21 ml) was added dropwise. After stirring for 10 minutes a solution of 5-hexylnyl p-toluenesulfonate (97.1 mmol) in tetrahydrofuran (200 ml) was added. The reaction mixture was stirred at room temperature for 18 hours, diluted with ether and the organic layer was washed with water and brine. The dried organic solution was concentrated and the product was purified by flash chromatography to give 1-phenylocta-1,7-diyne. A mixture of this compound (43 mmol), 2-bromobenzaldehyde (35.8 mmol), cuprous iodide (0.5 mmol) and bis(triphenylphosphine) palladium (II) chloride (0.7 mmol) in triethylamine (100 ml) was heated in an oil bath (95° C.) for one hour. The reaction mixture was cooled to 0° C., filtered and the filtrate was concentrated. The residue was dissolved in ether, washed with 10% hydrochloride acid, water and brine. The organic layer was dried and concentrated to give a product which was purified by flash chromatography to yield 2-(8-phenyl-1,7-octadiynyl)benzaldehyde. A solution of this compound (24.1 mmol) in ethyl acetate (100 ml) and 10% palladium on charcoal (1 g) was hydrogenated (40 psi of hydrogen) at room temperature for 15 minutes. The catalyst was filtered off and the filtrate concentrated to give the 2-(8-phenyloctyl)-benzaldehyde.

(c) Methyl 2-[2-(8-phenyloctyl)phenyl]-2-hydroxy acetate

The compound of Example 5(a) or 5(b) (10 mmol) was dissolved in methylene chloride (10 ml) and stirred at 0° C. under argon. Zinc iodide (1.1 mmol) was added followed by the dropwise addition of trimethylsilyl cyanide (1.45 ml, 11 mmol) dissolved in methylene chloride (20 ml). After 1 hour at 0° C. the ice bath was removed and the mixture stirred for 1 hour at room temperature. The solvent was stripped and methanol (60 ml) was added at ice bath temperature. Excess hydrogen chloride was bubbled into the solution while stirring. The ice bath was removed and the mixture stirred at room temperature for 18 hours. Water (12 ml) was added and the mixture stirred for 2 hours. The solvent was evaporated and the residue extracted with ethyl acetate, dried over anhydrous sodium sulfate, filtered and evaporated. The crude product was flash chromatographed on 200 grams of silica gel with 20% ethyl acetate/hexane as eluant to give the product as a clear colorless liquid.

(d) Methyl 2-chloro-2-[2-(8-phenyloctyl)-phenyl]acetate

The compound of Example 5(c) (6.8 mmol) was stirred under argon in an ice bath and thionyl chloride (15 ml) was added in a single portion. The ice bath was removed and the reaction mixture was stirred for 18 hours. The solvent was stripped and the residue flash chromatographed on 100 grams of silica gel with 20% methylene chloride/carbon tetrachloride as eluant to give the product as a clear colorless liquid.

(e) Methyl 2-[2-(8-phenyloctyl)phenyl]-2-[[1-(3-carboxylpropyl)-5-tetrazolyl]thio]acetate The compound of Example 5(d) (744 mg, 2 mmol) was dissolved in methylene chloride (25 ml) and stirred under argon at room temperature. 5-mercapto-1-(3-carboxypropyl)tetrazole (376 mg., 2 mmol) and triethylamine (0.84 ml, 6 mmol) were dissolved in methylene chloride (25 ml) and added to the solution of the compound of Example 5(d). The mixture was stirred under argon for 24 hours. The solvent was stripped and the residue was flash chromatographed on 100 grams of silica gel with 70:30:1 hexane:ethyl acetate:formic acid as eluant to give the desired product (830 mg, 79%).

(f) 2-[2-(8-phenyloctyl)phenyl]-2-[[1-(3-carboxypropyl)-5-tetrazolyl]thio]acetic acid.

The compound of Example 5(e) (524 mg, 1 mmol) was dissolved in methanol (12 ml) and stirred under argon in an ice bath, A 1 N solution of sodium hydroxide (4 ml, 4 mmol) was added dropwise, the ice bath removed, and the mixture stirred overnight at room temperature. The solvent was stripped and the residue was cooled in an ice bath and acidified with dilute hydrochloric acid. The crude product was extracted with ethyl acetate, dried over anhydrous sodium sulfate, filtered, and evaporated. The crude product was flash chromatographed on 70 grams of silica gel eluted with 30:70:1 ethyl acetate: hexane:formic acid followed by 50:50:1 ethyl acetate:hexane:formic acid to eluent to give the desired product (495 mg; 97%).

(g) 2-[2-(8-Phenyloctyl)phenyl]-2-[[1-(3-carboxypropyl)-5-tetrazolyl]thio]acetic acid, dipotassium salt, hydrate.

The compound of Example 5(f) (495 mg, 0.97 mmol) was treated with a solution of potassium carbonate (415 mg, 3 mmol) in 10 ml of water under argon at ice-bath temperature. The ice bath was removed and the mixture allowed to stir for 15 minutes at room temperature. The solution was then chromatographed on a $C_{18}$ column; elution was with water to remove the excess base and then with 1:1 (acetonitrile:water). Lyophilization gave the desired compound (524 mg, 92%) as a white hygroscopic solid.

Analysis for $C_{27}H_{32}N_4O_4S$ 2K $H_2O$— Calculated: C,53.62; H,5.67; N,9.26. Found: C,53.81; H,5.51; N,9.36.

Similarly the following compounds are prepared according to the general method of Example 5 from 2-(2-methoxyphenyl)-4,4-dimethyloxazoline and the appropriate alkyl halide;

2-[2-(4-phenylbutyl)phenyl]-2-[[1-(3-carboxypropyl)-5-tetrazolyl]thio]acetic acid, dipotassium salt, hydrate; and 2-[2-(10-phenyldecyl)phenyl]-2-[[1-(3-carboxypropyl)-5-tetrazolyl]thio]acetic acid, dipotassium salt, hydrate.

EXAMPLE 6

Preparation of 3-(2-Dodecylphenyl)-3-[[1-(3-(3-carboxypropyl)-5-tetrazolyl]thio]propanoic acid (a) t-Butyl 3-hydroxy-3-(2-dodecylphenyl)propionate A solution of diethylaluminum chloride (54.7 mmol) in hexane was added to a slurry of zinc dust (74.5 mmol) and a catalytic amount of copper (I) bromide (2.5 mmol) in anhydrous tetrahydrofuran (300 ml) while stirring under argon at 20° C. The resulting mixture was then cooled to 0° C. in an ice-methanol bath. A solution of t-butyl bromoacetate (49.8 mmol) and 2-dodecylbenzaldehyde of Example 1(c) (54.7 mmol); in anhydrous tetrahydrofuran was added slowly over 60 minutes. The reaction was stirred for about 24 hours and was permitted to warm slowly to room temperature. The mixture was filtered to remove zinc, concentrated, acidified with 3N hydrochloric acid and extracted with ether. Organic extracts were dried over magnesium sulfate, filtered, and evaporated to afford crude product. This material was then flash chromatographed on silica using 8% ethyl acetate in hexane to give the desired product in 79% yield.

(b) 3-(2-dodecylphenyl)-3-[[1-(3-carboxypropyl)-5-tetrazolyl]thio]propanoic acid.

A 3 neck 100 ml round bottom flask equipped with a thermometer and stirring bar was cooled to −30° C. using a dry ice-acetone bath followed by an ice-methanol bath. The flask was charged with trifluoroacetic acid (20 ml) followed by 5-mercapto-1-(3-carobxypropyl)tetrazole (0.00128 mol, 0.1923 g). The mixture was permitted to cool under argon for 10 minutes. To this was added the compound of Example 6(a) (0.001282 mol, 0.5 g), in methylene chloride (5 ml). The reaction was stirred for 2 hours at 15° C. and was permitted to warm to ambient temperature. The trifluoroacetic acid was evaporated and the resulting oil was chromatographed on $C_{18}$ packing using 20% water in methanol with 1.0% formic acid to yield the desired product.

Analysis for $C_{26}H_{40}N_4O_4S$— Calculated: (with 0.5 mole $H_2O$) C:60.81; H:7.79; N:10.92. Found: C:60.24; H:7.79; N:10.62.

Similarly, the following compounds are prepared according to the general method of Example 6.

3-(2-tetradecylphenyl)-3-[[1-(3-carboxypropyl)-5-tetrazolyl]thio]propanoic acid; and 3-(2-octylphenyl)-3-[[1-(3-carboxypropyl)-5-tetrazolyl]thio]propanoic acid.

EXAMPLE 7

Preparation of 3-[2-(8-Phenyloctyl)phenyl]-3-[(1-carboxymethyl-5-tetrazolyl)thio]propanoic acid (a) t-Butyl 3-hydroxy-3-[2-(8-phenyloctyl)phenyl]propionate A solution of diethlaluminum chloride (0.0082 moles, 8.2 ml) in hexane was added to a slurry of zinc dust (0.0111 mol: 0.7248 g) and a catalytic amount of copper (I) bromide (0.004 mol; 0.0585 g) in anhydrous tetrahydrofuran (40 ml) while stirring under argon at 20° C. the resulting mixture was then cooled to −20° C. in an ice-methanol bath. A solution of t-butyl bromoacetate (0.0082 mol; 1.32 ml) and 2-(8-phenyloctyl)benzaldehyde of Example 5(a) or (b) (0.0082 moles; 2.3969 g) in anhydrous tetrahydrofuran was added slowly over 60 min. The reaction was stirred overnight and was permitted to warm up slowly to room temperature. The mixture was filtered to remove zinc, concentrated, and azeotroped with methylene chloride. The resulting oil was then chromatographed on silica using 5% ethyl acetate in hexane with 0.5% formic acid to yield the desired product.

(b) Preparation of 3-[2-(8-phenyloctyl)phenyl]-3-[(1-carboxymethyl-5-tetrazolyl)thio]-propanoic acid A 3-neck 100 ml round bottom flask equipped with a thermometer and stirring bar was cooled to $-30°$ C. using a dry ice-acetone bath followed by an ice-methanol bath. The flask was charged with trifluoroacetic acid (10 ml) followed by 5-mercapto-1-carboxymethyltetrazole (0.00124 mol, 0.2 g). the mixture was permitted to cool under argon for 10 minutes. To this mixture was added the compound of Example 7(a) (0.00113 mol, 0.4634 g, in methylene chloride (3 ml). The reaction was stirred for 2 hours at $-15°$ C. and was then permitted to warm to room temperature. The trifluoroacetic acid was evaporated and azeotroped with methylene chloride. The resulting oil was chromatographed using 30% ethyl acetate in hexane with 0.5% formic acid to provide a 26% yield of desired product.

Analysis of $C_{26}H_{32}N_4O_4S \cdot 3/4H_2O$ — Calculated: C:61.21; H:6.32; N:10.98; S:6.29; Found: C:61.22; H:6.47; N:11.87; S:6.38

Similarly, the following compounds are prepared according to the general method of Example 7:

3-[2-(4-phenylbutyl)phenyl]-2-[(1-carboxypropyl-5-tetrazolyl)thio]propanoic acid; and 3-[2-(10-phenyldecyl)phenyl]-2-[(1-carboxypropyl-5-tetrozolyl)thio]propanoic acid.

EXAMPLE 8

Preparation of
3-[2-(8-Phenyl]-3-[[1-(3-carboxypropyl)-5-tetrazolyl]-thio]propanoic acid A 3-neck 100 ml round bottom flask equipped with a thermometer and stirring bar was cooled to $-30°$ C. using a dry ice-acetone bath followed by an ice-methanol bath. The flask was charged with trifluoroacetic acid (20 ml) followed by 5-mercapto-1-(3-carboxypropyl)tetrazole (0.0024 mol, 0.4574 g). The mixture was permitted to cool under argon for 10 minutes. To this was added the compound of Example 7(a) (0.0024 mol, 0.9069 g) in methylene chloride (5 ml). The reaction was stirred for 2 hours at $-15°$ C. and then was permitted to warm to room temperature. The trifluoroacetic acid was evaporated and the resulting oil was chromatographed on reverse phase $C_{18}$ packing using 20% water in methanol with 0.5% formic acid to give the desired product in 26% yield.

Analysis for $C_{28}H_{36}N_4O_4S \cdot \frac{1}{2}H_2O$ — Calculated: C:63.02; H:6.80; N:10.5. Found: C:63.08; H:6.74; N:10.4

EXAMPLE 9

Preparation of
2-(2-Undecyloxyphenyl)-2-[(1-carboxymethyl-5-tetrazolyl)thio]acetic acid (a) 2-Undecyloxybenzaldehyde To a stirred suspension of sodium hydride (10.0 mmol), which was prewashed with petroleum ether, in sieve dried dimethylformamide (10 ml) was added dropwise a solution of salicylaldehyde (10.1 mmol) in dimethylformamide (1 ml). To the reaction mixture was then added undecyl bromide (10.0 mmol) and the mixture stirred for 16 hours at ambient temperature under nitrogen. The reaction mixture was taken up in hexane (50 ml) and washed with 10 percent sodium hydroxide (2×50 ml) and saturated sodium chloride (50 ml). The organic phase was dried over anhydrous magnesium sulfate and charcoal. Evaporation of the volatiles yielded a colorless liquid which was purified by flash chromatography over silica gel with 2 percent ethyl acetate in hexane as eluant to afford the desired product as an oil.

Analysis for $C_{18}H_{28}O_2$: Calculated: C, 78.21; H, 10.21. Found: C, 77.92; H, 9.95.

(b) 2-(2-Undecyloxyphenyl)-2-[(1-carboxymethyl-5-tetrazolyl)thio]acetic acid

Employing the general methods of Example 1(d)–1(g), the compound of Example 9(a) is converted to the desired product.

The following compounds are prepared according to the general methods described above from the appropriately substituted hydroxybenzaldehyde and the appropriate alkyl halide:

2-(2-Heptyloxyphenyl)-2-[(1-carboxymethyl-5-tetrazolyl)thio]acetic acid;

2-(2-Dodecyloxyphenyl)-2-[(1-carboxymethyl-5-tetrazolyl)thio]acetic acid;

2-(5-Methoxy-2-dodecyloxyphenyl)-2-[(1-carboxymethyl-5-tetrazolyl)thio]acetic acid;

2-(5-Methyl-2-dodecyloxyphenyl)-2-[(1-carboxymethyl-5-tetrazolyl)thio]acetic acid;

2-(5-Fluoro-2-dodecyloxyphenyl)-2-[(1-carboxymethyl-5-tetrazolyl)thio]acetic acid;

2-(5-Chloro-2-dodecyloxyphenyl)-2-[(1-carboxymethyl-5-tetrazolyl)thio]acetic acid;

2-(5-Iodo-2-dodecyloxyphenyl)-2-[(1-carboxymethyl-5-tetrazolyl)thio]acetic acid;

2-(5-Bromo-2-dodecyloxyphenyl)-2-[(1-carboxymethyl-5-tetrazolyl)thio]acetic acid;

2-(5-Hydroxy-2-dodecyloxyphenyl)-2-[(1-carboxymethyl-5-tetrazolyl)thio]acetic acid;

2-(5-Nitro-2-dodecyloxyphenyl)-2-[(1-carboxymethyl-5-tetrazolyl)thio]acetic acid;

2-(5-Amino-2-dodecyloxyphenyl)-2-[(1-carboxymethyl-5-tetrazolyl)thio]acetic acid; and 2-(5-Trifluoromethyl-2-dodecyloxyphenyl)-2-[(1-carboxymethyl-5-tetrazolyl)thio]acetic acid;

2-(2-Dodecylthiophenyl)-2-dodecyloxyphenyl)-2-[(1-carboxymethyl-5-tetrazolyl)thio]acetic acid is prepared from 2-(dodecylthio)benzaldehyde.

2-(2-Heptylthiophenyl)-2-[(1-carboxymethyl-5-tetrazolyl)thio]acetic acid is prepared from 2-(heptylthio) benzaldehyde.

EXAMPLE 10

Preparation of
2-[2-6-Phenylhexyloxy)phenyl]-2-[[1-(3-carboxypropyl-5-tetrazolyl)thio]acetic acid a) 2-(6-Phenylhexyloxy)benzaldehyde A solution of 6-phenylhexanoic acid (19.8 mmol) in sieve dried tetrahydrofuran (5 ml) was reduced with diborane in tetrahydrofuran (30 ml, 29.1 mmol) at 0° C. for 4 hours to give 6-phenylhexanol. To an ice cold solution of the hexanol (ca. 19.8 mmol) and carbon tetrabromide (21.98 mmol) in methylene chloride (50 ml) was added triphenylphosphine (22.30 mmol) in methylene chloride (50 ml) and the resulting solution was stirred for 2.5 hours. The volatiles were evaporated and the residue was taken up in either (100 ml), cooled in ice, and filtered. The filtrate was evaporated and distilled to afford 6-phenylhexyl bromide as an oil. A mixture of the bromide (8.00 mmol), salicylaldehyde (8.19 mmol) and potassium carbonate (9.33 mmol) in dimethylformamide (10 ml) was heated to 100° C. and maintained at that temperature for one hour. The cooled reaction mixture was taken up in hexane (50 ml) and washed with 5% sodium hydroxide (50 ml) and saturated sodium chloride (50 ml). The organic phase was dried over anhydrous magnesium sulfate and charcoal. Evaporation yielded a colorless oil which was purified by flash chromatography over silica gel with 5% ethyl acetate in hexane as eluant to afford the desired product as an oil.

Analysis for $C_{19}H_{22}O_2$: Calculated: C, 80.82; H, 7.85. Found: C, 80.62; H, 7.72.

(b) 2-[2-(6-Phenylhexyloxy)phenyl]-2-[[1-(3-carboxypropyl)-5-tetrazolyl]thio]acetic acid Employing the general methods of Example 5(c) through 5(g) the compound of Example 10(a) is converted to the desired product.

The following compounds are prepared according to the general methods described above from the appropriately substituted phenylalkyloxy benzaldehyde.

2-[2-(3-Phenylpropyloxy)phenyl]-2-[[1-(3-carboxypropyl)-5-tetrazolyl]thio]acetic acid; and
2-[2-(9-Phenylnonyloxy)phenyl]-2-[[1-(3-carboxypropyl)-5-tetrazolyl]thio]acetic acid.

EXAMPLE 11

Preparation of
2-Methyl-3-(2-dodecylphenyl)-3-[(1-carboxymethyl-5-tetrazolyl)thio]propanoic acid (a) Methyl 2-methyl-3-hydroxy-3-(2-dodecylphenyl)-propanoate To a suspension of zinc dust (15 mmol) and copper (I) bromide (5 mmol) in distilled tetrahydrofuran (10 ml) at 25° C. was added diethylaluminum chloride (10 mmol). The mixture was stirred for 5 minutes, then cooled to 0° C. in an ice-methanol bath. A solution of the compound of Example 1(c) (10 mmol) and methyl dl-2-bromopropionate (10 mmol) in tetrahydrofuran (10 ml) was added dropwise to the cold suspension. The resulting mixture was stirred for 3 hours at 25° C. The reaction mixture was filtered and the filtrate was washed with water, dried over magnesium sulfate, and evaporated to give the product.

(b) Methyl 3-(2-dodecylphenyl)-3-[(1-carbethoxymethyl-5-tetrazolyl)thio]propanoate To a solution of trifluoroacetic acid (15 ml) and 5-mercapto-1-carbethoxymethyltetrazole (2.4 ml) at 0° C. is added the compound of Example 11(a). The reaction mixture stirred for 3 hours and evaporated. The resulting residue is flash chromatographed on silica, and eluted with 20% ethyl acetate in hexane, to give the product.

(c) 2-Methyl-3-(2-dodecylphenyl)-3-[(1-carboxymethyl-5-tetrazolyl)thio]-propanoic acid To a solution of 10% sodium hydroxide (50 ml), methanol (12 ml) and ethylene glycol dimethyl ether is added the compound of Example 12(b) (93.9 mmol). The mixture is stirred for 24 hours at 25° C. The reaction mixture is then cooled in an ice-methanol bath to 0° C. and is acidified with hydrochloric acid to pH 3.5, is extracted with diethyl ether, is dried over magnesium sulfate, filtered and evaporated. The resulting mixture of isomers is flash chromatographed on silica, and eluted with 30% ethyl acetate in hexane, to give the product.

EXAMPLE 12

Preparation of
2-(2-dodecylphenyl)-2-[2-(tetrazol-5-yl)ethylthio]acetic acid (a) 5-(2-Mercaptoethyl)tetrazole To 100 ml of tetrahydrofuran at 0° was added aluminum chloride (6.65 g, 0.05 mol) and sodium azide (9.75 g, 0.15 mol). This mixture was allowed to come to 22°, and stirred 30 minutes. β-Mercaptopropionitrile (4.35 g, 0.05 mol) was added, and the mixture heated to reflux for 24 hr. The mixture was cooled, acidified carefully with excess 15% aqueous hydrochloric acid, and the solvents removed under reduced pressure. The residue was extracted with ethyl acetate, the extracts washed with water, dried, and the solvent evaporated. The residue was recrystallized from 1,2-dichloroethane, and gave 3.7 g (57%) of 5-(2-mercaptoethyl)tetrazole.

EXAMPLE 12

Preparation of
2-(2-dodecylphenyl)-2-[2-(tetrazol-5-yl)ethylthio]acetic acid (a) 5-(2-Mercaptoethyl)tetrazole To 100 ml of tetrahydrofuran at 0° was added aluminum chloride (6.65 g, 0.05 mol) and sodium azide (9.75 g, 0.15 mol). This mixture was allowed to come to 22°, and stirred 30 minutes. β-Mercaptopropionitrile (4.35 g, 0.05 mol) was added, and the mixture heated to reflux for 24 hr. The mixture was cooled, acidified carefully with excess 15% aqueous hydrochloric acid, and the solvents removed under reduced pressure. The residue was extracted with ethyl acetate, the extracts washed with water, dried, and the solvent evaporated. The residue was recrystallized from 1,2-dichloroethane, and gave 3.7 g (57%) of 5-(2-mercaptoethyl)tetrazole.

(b) Methyl 2-(2-dodecylphenyl)-2-[2-(tetrazol-5-yl)ethylthio]acetate

A mixture of methyl 2-chloro-2-(2-dodecyl phenyl)acetate (0.615 g, 1.75 mmol), 5-(2-mercaptoethyl)-tetrazole (0.227 g, 1.75 mmol), and triethylamine (0.48 ml), 3.5 mmol) in 20 ml of methylene chloride was stirred 18 hours at 22° and the solvent was evaporated. The residue taken up in diethyl ether, washed with 1 N hydrochloric acid, dried and the solvent removed. The residue was chromatographed over a silica gel column. Impurities were eluted with ethyl acetate/hexane (1:3), and the product was eluted with methanol/ethyl acetate (1:19). Evaporation of the solvents from these fractions gave the desired product, 0.570 g (73%).

(c) 2-(2-Dodecylphenyl)-2-[2-(tetrazol-5-yl)-ethylthio]acetic acid

A stirred suspension of methyl 2-(2-dodecyl-phenyl)-2-[2-tetrazol-5-yl)ethylthio]acetate (0.57 g, 1.28 mmol) in 10 ml of methanol and 8 ml of water at 70° was treated with 3 ml of 2.5 N sodium hydroxide. After 30 minutes at 70°, the mixture was cooled, diluted with 10 ml of water and filtered. The filtrate was acidified, extracted with ethyl acetate, and the extracts were dried and the solvent evaporated. The residue was recrystallized from methanol and gave the desired product 0.415 g (74%). NMR (CDCl$_3$/Me$_2$CO): 10.23–11.70 (broad,2H), 7.52–7.62 (m,1H), 7.27 (s,3H), 5.04 (s,1H), 3.0–3.44 (m,4H), 2.63–2.92 (t,2H), 1.12–1.84 (m,20H), 0.62–1.02 (t,3H).

EXAMPLE 13

Preparation of
3-[2-(8-phenyloctyl)phenyl]-3-[[1-(3-carboxypropyl)-5-tetrazolyl]thio]-2-hydroxypropanoic acid (a) 2-(8-Phenyloctyl)benzaldehyde 2-(8-phenyloctyl)benzaldehyde was prepared as described in Example 5(a) or (b).

(b) Methyl 3-[2-(8-Phenyloctyl)phenyl]-2,3-epoxypropionate

The compound of Example 7(a) (2.94 g, 10 mmol) was dissolved in diethyl ether (25 ml) and the solution was stirred under argon at 0° C. Methyl chloroacetate (1.32 ml, 15 mmol) was added, followed by the addition of sodium methoxide (810 mg, 15 mmol). the mixture was stirred for 2.5 hours at ice bath temperature. A small quantity of water was added, the ether phase separated, dried over anhydrous sodium sulfate, filtered and evaporated. The residue was flash chromatographed on 80 grams of silica gel eluted with 5–30% ethyl acetate/hexane to give the product.

(c) Methyl 3-[2-(8-phenyloctyl)phenyl]-3-[[1-(3-carboxypropyl-5-tetrazolyl]thio]-2-hydroxypropionate The compound of Example 13(c) (549 mg, 1.5 mmol) was dissolved in methanol (6 ml) containing 2% triethylamine and the solution was stirred under argon at room temperature. The 5-mercapto-1-(3-carobxypropyl)-tetrazole (282 mg, 1.5 mmol) and triethylamine (0.84 ml, 6 mmol) were dissolved in methanol (9 ml) and added dropwise to the reaction mixture which was then stirred for 5 days at room temperature. The solvent was stripped and the residue was flash chromatographed on 50 grams of silica gel eluted with 70:30:1 (hexane:ethyl acetate:formic acid) to give the desired product.

(d) 3-[2-(8-phenyloctyl)phenyl]-3-[[1-(3-carboxypropyl)-5-tetrazolyl]thio]-2-hydroxypropanoic acid The compound of Example 13(d) (554 mg, 1 mmol) was dissolved in methanol (15 ml) and stirred under argon at ice bath temperature. A 1 N solution of sodium hydroxide (4 ml, 4 mmol) was added dropwise, the ice bath removed and the mixture stirred at room temperature overnight. The methanol was stripped and the residue acidified with dilute hydrochloric acid. Extraction with ethyl acetate followed by drying over anhydrous sodium sulfate, filtration and evaporation gave the crude product which was flash chromatographed on 25 grams of silica gel eluted with 50:50:1(ethyl acetate:hexane:formic acid) to give the desired product.

EXAMPLE 14

Preparation of
3-[2-(8-phenyloctyl)phenyl]-3-[(1-carboxymethyl-5-tetrazolyl)thio]-2-hydroxypropanoic acid (a) Methyl 2,3-epoxy-3-[2-(8-phenyloctyl)phenyl]-propanoate 2-(8-phenyloctyl)benzaldehyde prepared as in Example 5(a) or (b) (15 g) was dissolved in methylene chloride (58 ml) under an argon atmosphere at 25° C. Methyl chloroacetate (6.2 ml) was added in one portion. The resulting solution was cooled to −28° C. using a dry ice/isopropanol bath. Sodium methoxide (13.5 ml) was then added slowly, maintaining temperature between −28° C. to −15° C. The reaction mixture was then stirred for 45 minutes, and permitted to warm slowly to 0° C. The reaction was then stirred for 1.5 ours at 0° C. The reaction mixture was quenched with a solution (117 ml) of aqueous buffer (pH 7) and 117 ml of hexane. The layers were separated, the aqueous portion was filtered and washed with hexane. The combined organic extracts were dried over sodium sulfate, filtered and concentrated. The residue was flash chromatographed on silica and eluted with 3:97 ethyl acetate/hexane to give the desired product.

(b) Methyl 2-hydroxy-3-[(1-carobxymethyl-5-tetrazolyl)thio]propanoate

The methyl 2,3-epoxy-3-[2-(8-phenyloctyl)-phenyl]-propanoate (0.4 g) of Example 14(a) was dissolved in 5 ml of methanol containing 2% triethylamine under an argon atmosphere. The reaction mixture was cooled using an ice/methanol bath. A solution of 0.205 g of 5-mercapto-1-carbethoxymethyltetrazole and 0.61 ml of triethylamine in 5 ml of methanol containing 2% triethylamine was added. The bath was removed and the reaction was permitted to warm to room temperature. The reaction was concentrated and flash chromatographed on silica with 20% ethyl acetate/hexane as eluant to give the desired product.

(c) 3[2-(8-phenyloctyl)phenyl]-3-[(1-carboxymethyl-5-tetrazolyl)thio]-2-hydroxy propanoic acid The methyl 2-hydroxy-3-[(1-carboxymethyl-5-tetrazolyl)thio]propanoate (0.45 g) of Example 14(b) was dissolved in methanol (6.6 ml) and cooled with an ice and methanol bath to which was added 3.3 ml of a 4% solution of sodium hydroxide. The bath was removed and reaction permitted to warm to room temperature overnight. The methanol was then stripped, and the residue was diluted with dilute hydrochloric acid. Extraction with ethyl acetate was followed by drying over magnesium sulfate, filtration, and evaporation. The crude product was flash chromatographed on silica with 30–50% ethyl acetate/hexane. The column was washed with 100% methanol. 40 mg of desired product was recovered.

EXAMPLE 15

Preparation of
2-(2-Dodecylphenyl)-2-(5-carboxy-4-methyl-2-thiazolylthio)acetic acid (a) Methyl 2-(2-Dodecylphenyl)-2-(5-carbomethoxy-4-methyl-2-thiazolylthio)acetate A mixture of 0.53 g (0.0015 mol) of the compound of Example 1(e), 0.39 g (0.0015 mol) of the compound of Example 1(e), 0.39 g (0.00195 mol) of methyl 4-methyl-2-mercaptothiazole-5-caroxyplate, 0.23 g (0.0023 moles) of triethylamine and 10 ml of methylene chloride were stirred under argon at room temperature for 48 hours. The reaction mixture was washed 3 times with 5 ml of 5% sodium carbonate solution followed by water, dried over magnesium sulfate, filtered and concentration under vacuum. The oily residue was flash chromatographed using hexane—5% ethyl acetate yielding 0.58 g of oil.

(b) 2-(2-Dodecylphenyl)-2-(5-carboxy-4-methyl-2-thiazolylthio)acetic acid

A mixture of 0.24 g (0.0046 mol) of the compound of Example 15(a), 0.11 g (0.0028 mol) of sodium hydroxide, 10 ml of methanol and 1 ml of water were stirred at room temperature and under argon for 2 days. The reaction mixture was concentrated under vacuum and the residual oil was redissolved in 5 ml of water. The aqueous solution was adjusted to pH 3.83 with dilute phosphoric acid or until a cloudy solution was obtained;

and then was extracted 3 times with 10 ml of ethyl acetate. The extracts were washed with 5 ml of water, dried over magnesium sulfate, filtered and concentrated. The oily residue obtained was triturated with petroleum ether. The desired product (0.054 g) was obtained as a powder having a m.p. of 88°–91° C.

Analysis for $C_{25}H_{35}NO_4S_2$: Calculated: C:62.86; H:7.38; N:2.93; Found: C:62.59; H:7.47; N:2.88.

EXAMPLE 16

Preparation of 2-[2-(8-phenyloctyl)phenyl]-2-[[2-carboxy-5-(1,3,4-thiadiazolyl)]thio]acetic acid (a) Methyl 2-[2-(8-phenyloctyl)phenyl]-2-]]2-carbethoxy-5-(1,3,4-thiadiazolyl)]thio]-acetate The compound of Example 5(d) (744 mg, 2 mmol) is dissolved in 25 ml of methylene chloride and stirred under argon at room temperature. Ethyl 5-mercapto-1,3,4-thiadiazole-2-carboxylate (380 mg. 2 mmol) and triethylamine (0.84 ml, 6 mmol) is dissolved in 25 ml of methylene chloride and added to the solution of the compound of Example 5(d). The mixture is stirred under argon for 48 hours. The solvent is evaporated, and the residue is flash chromatographed on silica gel eluted with ethyl acetate/hexane to give the product.

(b) 2-[-2-(8-phenyloctyl)phenyl]-2-[[2-carboxy-5-(1,3,4-thiadiazolyl)]thio]acetic acid The compound of Example 16(a) (526 mg, 1 mmol) is dissolved in 10 ml of methanol and stirred under argon in an ice bath. A 1 N solution of sodium hydroxide (4 ml, 4 mmol) is added. The ice bath is removed and the mixture is stirred for 24 hours at room temperature. The solvent is evaporated, the residue cooled in an ice bath, acidified with dilute hydrochloric acid, extracted with ethyl acetate, dried over anhydrous sodium sulfate, filtered and evaporated to give the product.

EXAMPLE 17

Preparation of 2-[2-(8-phenyloctyl)phenyl]-2-[(2-carboxy-5-furfuryl)thio]acetic acid (a) Methyl 2-[2-(8-phenyloctyl)phenyl]-2-[(2-carboxy-5-furfuryl)thio]acetate The compound of Example 5(d) (744 mg, 2 mmol) is dissolved in 25 ml of methylene chloride and stirred under argon at room temperature. 5-mercaptomethylfuroic acid (316 mg, 2 mmol) and triethylamine (0.84 ml, 6 mmol) is dissolved in 25 ml of methylene chloride and added to the solution of the compound of Example 5(d). The mixture is stirred under argon for 48 hours. The solvent is evaporated, and the residue is flash chromatographed on silica gel eluted with ethyl acetate/hexane/formic acid to give the product.

(b) 2-[2-(8-phenyloctyl)phenyl]-2-[(2-carboxy-5-furfuryl)thio]acetic acid

The compound of Example 17(a) (494 mg, 1 mmol) is dissolved in 10 ml of methanol and stirred under argon in an ice bath. A 1 N solution of sodium hydroxide (4 ml, 4 mmol) is added. The ice bath is removed and the mixture is stirred for 24 hours at room temperature. The solvent is evaporated, the residue cooled in an ice bath, acidified with dilute hydrochloric acid, extracted with ethyl acetate, dried over anhydrous sodium sulfate, filtered and evaporated to give the product.

EXAMPLE 18

Preparation of 3-[2-(6-thiophenoxyhexylthio)phenyl]-3-[[1-(3-carboxypropyl)-5-tetrazolyl]thio]-2-hydroxypropanoic acid a) Preparation of 2-(6-thiophenoxyhexylthio)-benzoic acid Thiosalicylic acid (1.2 g, 0.008 mole) and 6-thiophenoxyhexylbromide (2.5 g, 0.009 mole) are dissolved in dimethylformamide (50 ml) and the solution is stirred under argon. Potassium carbonate (1.5 g, 0.011 mole) is added carefully to the reaction. After the addition is complete the mixture is slowly warmed to 100° C. The solvents are evaporated, and the residue is dissolved in water, acidified with dilute hydrochloric acid, extracted with ethyl acetate, dried over anhydrous sodium sulfate, filtered, and evaporated. The residue is flash chromatographed on silica gel to give the desired product.

(b) Preparation of 2-(6-thiophenoxyhexyl-thio)benzyl alcohol.

To a suspension of lithium aluminum hydride (0.292 g, 0.007 mole) in tetrahydrofuran (30 ml) is added a solution of 2-(6-thiophenoxyhexylthio)benzoic acid (2.42 g, 0.007 mole) in tetrahydrofuran (30 ml). The reaction is conducted as in Example 1b).

(c) Preparation 2-(6-thiophenoxyhexylthio)-benzaldehyde

To a suspension of manganese dioxide (11.78 g, 0.135 mole) in ethyl acetate (30 ml) is added a solution of 2-(6-thiophenoxyhexylthio)benzyl alcohol (1.23 g; 0.0037 mole) in ethyl acetate (20 ml). The reaction is conducted as in Example 1c).

(d) Methyl 3-[2-(6-thiophenoxyhexylthio)-phenyl]-2,3-epoxypropionate

The compound of Example 18(c) (10 mmol) is dissolved in diethyl ether (25 ml) and the solution is stirred under argon at 0° C. Methyl chloroacetate (15 mmol) is added followed by the addition of sodium methoxide (15 mmol). The mixture is stirred for 2.5 hours at ice bath temperature. A small quantity of water is added, the ether phase is separated, dried over anhydrous sodium sulfate, filtered, and evaporated. The residue is flash chromatographed on 80 grams of silica gel eluted with 5–30% ethylacetate/hexane to give the product.

(e) Methyl 3-[2-(6-thiophenoxyhexylthio)-phenyl]-3-[[-3-]]1-(3-carboxypropyl-5-tetrazolyl]thio]-2-hydroxypropionate The compound of Example 18(d) (1.5 mmol) is dissolved in methanol (6 ml) containing 2% triethylamine and the solution is stirred under argon at room temperature. 5-Mercapto-1-(3-carboxypropyl)tetrazole (1.5 mmol) and triethylamine (6 mmol) are dissolved in methanol (9 ml) and are added dropwise to the reaction mixture which is then stirred for 5 days at room temperature. The solvent is stripped and the residue is flash chromatographed on 50 grams of silica gel eluted with 70:30:1 (hexane:ethylacetate:formic acid) to give the desired product.

f) 3-[2-(6-thiophenoxyhexylthio)phenyl]-3-[[1-(3-carboxypropyl)-5-tetrazolyl]-thio]-2-hydroxypropanoic The compound of Example 18(e) (1 mmol) is dissolved in methanol (15 ml) and is stirred under argon at ice bath temperature. A 1N solution of sodium hydroxide 94 mmol) is added dropwise, the ice bath is removed and the mixture is stirred at room temperature overnight. The methanol is stripped and the residue is acidified with dilute hydrochloric acid. Extraction with ethyl acetate followed by drying over anyhydrous sodium sulfate, filtration, and evaporation gives the crude product which is flash chromatographed on 25 grams of silica gel eluted with 50:50:1 (ethyl acetate:hexane:formic acid) to give the desired product.

EXAMPLE 19

As a specific embodiment of a composition of this invention, an active ingredient, such as the compound of Example 4, 13, or 14 is dissolved in isotonic saline at a concentration of 1 to 10 mg/ml and aerosolized from a nebulizer operating at an air flow adjusted to deliver the desired aerosolized weight of drug.

EXAMPLE 20

As an additional embodiment of a composition of this invention 100 to 1000 mg of an active ingredient, such as the compound of Example 4, 13, or 14 is combined with 4 mg of chlorpheniramine maleate with a suitable carrier or excipient.

What is claimed is:

1. A compound of formula (I)

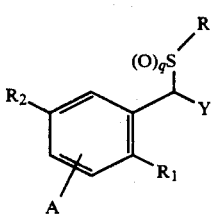

wherein
q is 0, 1, or 2;
$R_1$ is $(L)_a\text{-}(CH_2)_b\text{-}(T)_c\text{-}B$ wherein
a is 0 or 1;
b is 3 or 14;
c is 0 or 1;
L and T are independently oxygen, sulfur, or $CH_2$ with the proviso that L and T are not sulfur when q is 1 or 2;
B is $C_{1-4}$ alkyl, ethynl, trifluoromethyl, isopropenyl, furanyl, thienyl, cyclohexyl, or phenyl optionally monosubstituted with Br, Cl, $CF_2$, $C_{1-4}$ alkyl, $C_{1-4}$ alkoxy, methylthio, or trifluoromethylthio;
$R_2$ and A are independently selected from H, $CF_3$, $C_{1-4}$ alkyl, $C_{1-4}$ alkoxy, F, Cl, Br, I, OH, $NO_2$ or $NH_2$; or
$R_1$ and A are H and $R_2$ is $(L)_a\text{-}(CH_2)_b\text{-}(T)_c\text{-}B$ wherein a, b, c, L, T, and B are as defined above;
Y is

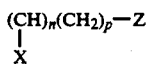

wherein
$R_3$ is OH, $NH_2$, aryloxy or $C_{1-6}$ alkoxy;

n is 0 or 1;
p is 0 or 1;
x is H, OH, $C_{1-4}$ alkyl, $C_{1-4}$ alkoxy, or F; and
Z is $COR_3$, or tetrazolyl;
R is

m is 0 to 6;
$R_4$ and $R_5$ are independently hydrogen or $C_{1-4}$ alkyl at any position when m is not 0;
W is unsubstituted or substituted with one to three

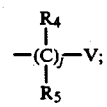

$R_4$ and $R_5$ are as defined above;
j is 0 to 6; and
V is hydrogen, $C_{1-4}$ alkyl, $COR_3$, $SO_3H$, $SO_2H$, $SO_2NH_2$, $COCH_2OH$, $CHOHCH_2OH$, or tetrazolyl, with $R_3$ as defined above; or a pharmaceutically acceptable salt thereof.

2. A compound of claim 1 wherein Y is COOH.

3. A compound of claim 2 wherein $R_1$ is $C_8$ to $C_{14}$ alkyl or phenyl $C_4$ to $C_{10}$ alkyl.

4. A compound of claim 3 where m is 0 and W is thiadiazolyl the compound 2-[2-(8-phenyloctyl)phenyl)-2-[[2-carboxy-(1,3,4-thiadiazolyl)]thio]acetic acid, or a pharmaceutically acceptable salt thereof.

5. A compound of claim 1 wherein Y is $CH_2COOH$.

6. A compound of claim 5 wherein $R_1$ is $C_8$ to $C_{14}$ alkyl or phenyl $C_4$ to $C_{10}$ alkyl.

7. A compound of claim 1 wherein Y is CH(OH)-COOH.

8. A compound of claim 7 wherein $R_1$ is $C_8$ to $C_{14}$ alkyl or phenyl $C_4$ to $C_{10}$ alkyl.

9. A pharmaceutical composition comprising a pharmaceutical carrier or diluent and a compound of claim 1.

10. A pharmaceutical composition according to claim 9 in the form of an aerosol formulation or a sterile solution, or in a form suitable for administration by inhalation, parenteral administration, or topical administration.

11. A pharmaceutical composition comprising a pharmaceutical carrier or diluent a compound of claim 9 and an histamine H1-receptor antagonist.

12. A method for inhibiting the effects of leukotrienes comprising administrating an effective amount of the composition of claim 9.

13. A method for inhibiting antigen-induced respiratory anaphylaxis comprising administrating an effective amount of the composition of claim 9.

* * * * *

UNITED STATES PATENT AND TRADEMARK OFFICE
CERTIFICATE OF CORRECTION

PATENT NO. : 5,135,938

DATED : August 4, 1992

INVENTOR(S) : John G. Gleason, Ralph F. Hall and Irene Uzinskas

It is certified that error appears in the above-identified patent and that said Letters Patent is hereby corrected as shown below:

At Column 30, line 15 should read "W is <u>thiadiazolyl</u> unsubstituted or substituted with one to three..."

Signed and Sealed this

Thirtieth Day of November, 1993

Attest:

BRUCE LEHMAN

Attesting Officer

Commissioner of Patents and Trademarks